(12) United States Patent
Mertelmeier

(10) Patent No.: US 6,999,554 B2
(45) Date of Patent: Feb. 14, 2006

(54) X-RAY DIAGNOSTIC APPARATUS FOR MAMMOGRAPHY EXAMINATIONS

(75) Inventor: Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/991,242

(22) Filed: Nov. 17, 2004

(65) Prior Publication Data

US 2005/0129172 A1    Jun. 16, 2005

(30) Foreign Application Priority Data

Nov. 17, 2003   (DE) ................................ 103 53 611

(51) Int. Cl.
*A61B 6/04* (2006.01)
*H05G 1/02* (2006.01)

(52) U.S. Cl. .................... 378/37; 378/196; 378/197
(58) Field of Classification Search .............. 378/37, 378/39, 45, 46, 196–198, 205
See application file for complete search history.

(56) References Cited

U.S. PATENT DOCUMENTS

| | | | |
|---|---|---|---|
| 4,727,565 A | * | 2/1988 | Ericson ...................... 378/205 |
| 4,926,453 A | | 5/1990 | Toniolo |
| 5,018,176 A | * | 5/1991 | Romeas et al. .............. 378/37 |
| 5,594,769 A | * | 1/1997 | Pellegrino et al. ............ 378/37 |
| 5,872,828 A | | 2/1999 | Niklason et al. |
| 5,964,715 A | * | 10/1999 | Thunberg ................... 600/562 |
| 6,442,288 B1 | | 8/2002 | Haerer et al. |
| 6,740,882 B1 | | 5/2004 | Weinberg |

FOREIGN PATENT DOCUMENTS

| | | |
|---|---|---|
| EP | 0 370 089 | 9/1994 |
| WO | WO 90/05485 | 5/1990 |

* cited by examiner

*Primary Examiner*—Craig E. Church
*Assistant Examiner*—Irakli Kiknadze
(74) *Attorney, Agent, or Firm*—Schiff Hardin LLP

(57) ABSTRACT

A x-ray diagnostic apparatus for mammography examinations has a support arm is supported in a bearing such that it can pivot around a substantially horizontal axis, and on which are arranged an arm provided with an x-ray source, a mounting provided with an x-ray receiver and a compression device. The arm, the mounting and the compression device can be mutually pivoted with the support arm around the horizontal axis. Additionally the arm and the mounting can be pivoted relative to the compression device around the horizontal axis and the arm can be pivoted relative to the mounting and the compression device around the horizontal axis.

21 Claims, 5 Drawing Sheets

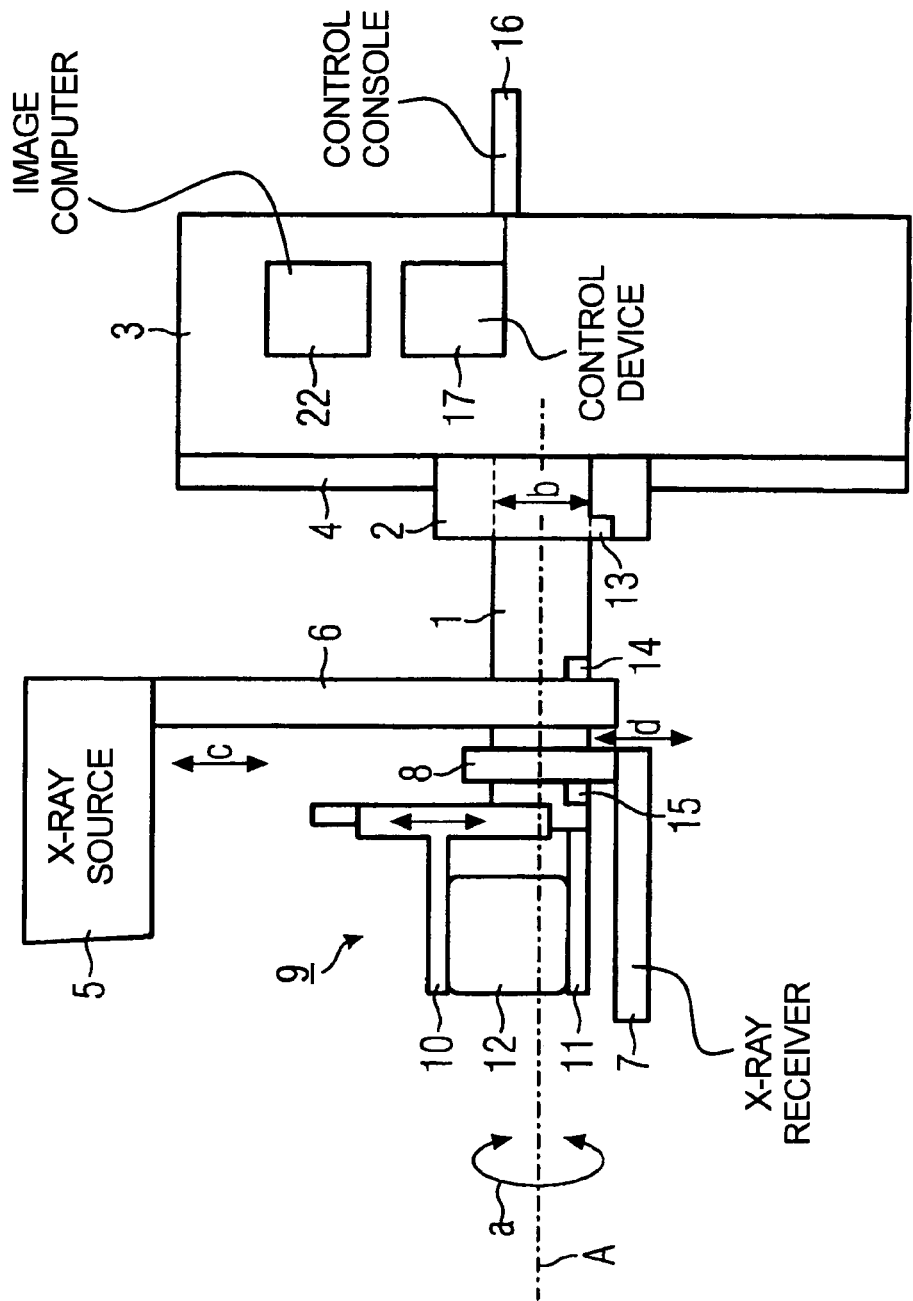

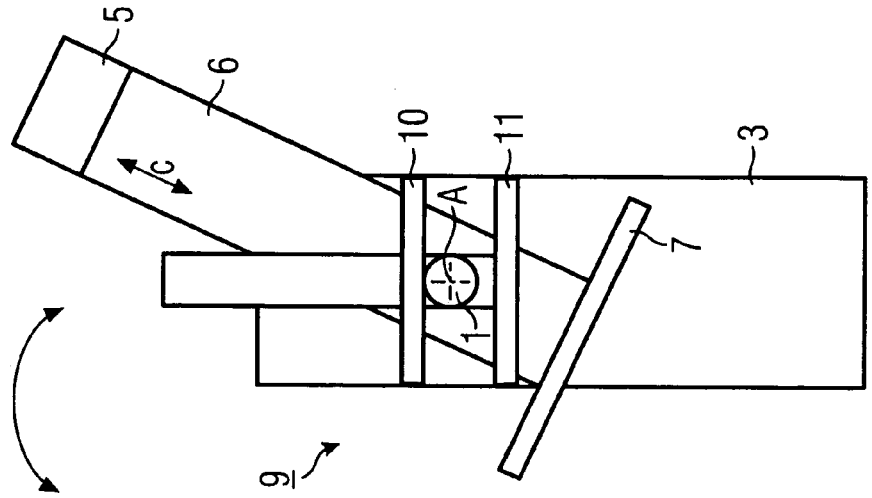
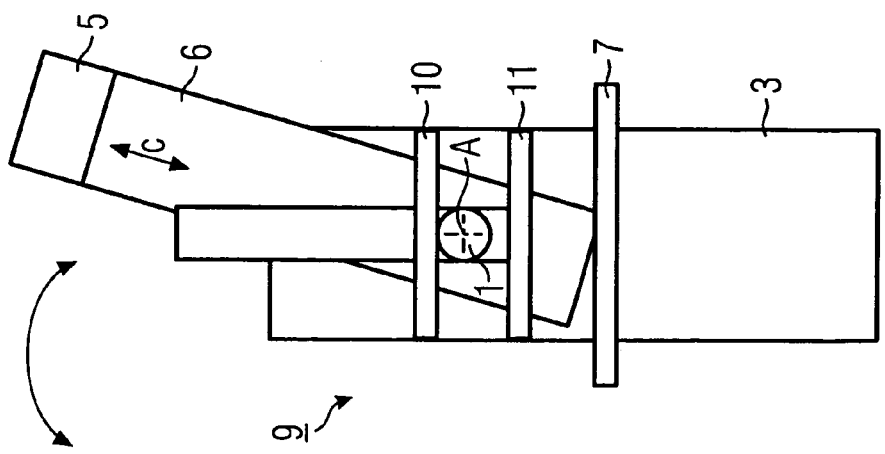

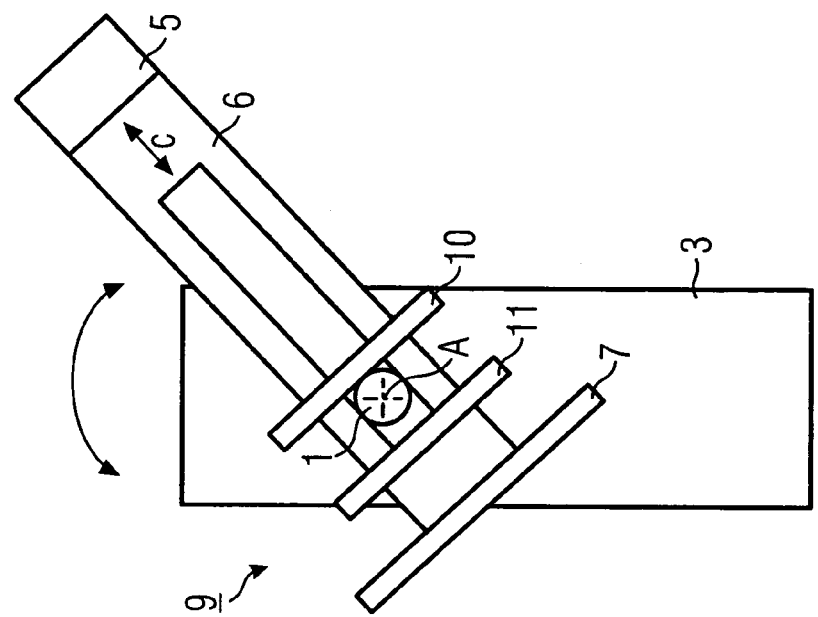
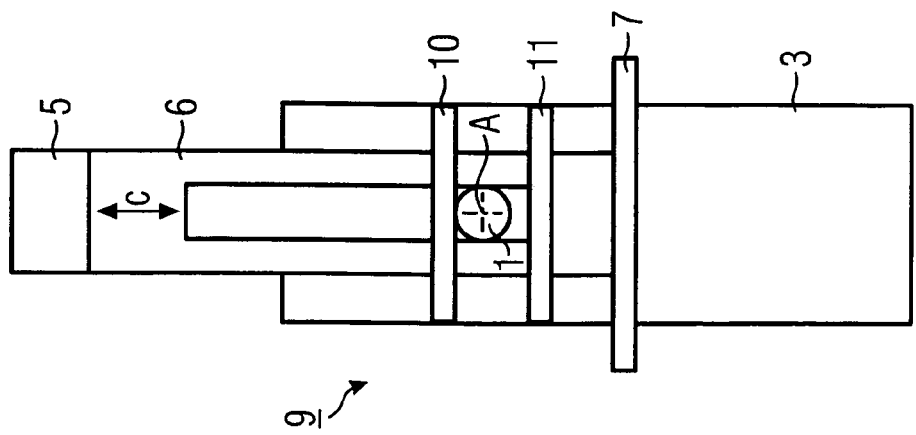

X-RAY DIAGNOSTIC APPARATUS FOR MAMMOGRAPHY EXAMINATIONS

BACKGROUND OF THE INVENTION

1. Field of the Invention

The present invention concerns an x-ray diagnostic apparatus for mammography examinations of the type having a support arm which in one bearing is supported so as to pivot around a substantially horizontal axis, and with which an x-ray source, an x-ray receiver and a compression device are connected, such that the x-ray source, the x-ray receiver and the compression device can be mutually pivoted with the support arm around the horizontal axis.

2. Description of the Prior Art

An x-ray diagnostic apparatus of the above type is specified in European Application 0 370 089. This x-ray diagnostic apparatus has a support arm that can be pivoted around a horizontal axis, a compression device for a female breast disposed on the support arm. Furthermore, a frame on which an x-ray source and an x-ray receiver are arranged opposite one another is connected with the support arm. The frame can be displaced in guides in a straight line relative to the support arm and the compression device, such that enlarged exposures of a breast compressed with the compression device are enabled. The pivot axis is disposed relative to the compression device such that is essentially aligned with the central breast axis of the compressed female breast. X-ray exposures of a compressed breast can thereby be acquired from various directions by means of mutual pivoting of the x-ray source, the x-ray receiver and the compression device around the horizontal axis, without having to significantly shift the patient.

An x-ray diagnostic apparatus for mammography examinations is known from U.S. Pat. No. 4,727,565 wherein a frame provided with an x-ray source and an x-ray receiver is disposed on a support arm that can be pivoted around a horizontal axis and can be pivoted relative to a compression device in order to be able to acquire x-ray exposures from various directions of a compressed breast that is held stationary. The mutual pivoting of the x-ray source and the x-ray receiver around the compression device that is stationary relative to the x-ray source and the x-ray receiver during x-ray exposures enables acquisition of spatial information of tissue to be examined in the compressed breast for the implementation of a biopsy.

U.S. Pat. No. 5,872,828 discloses positioning an x-ray source of an x-ray diagnostic apparatus for tomosynthesis for mammography examinations such that it can be pivoted around a horizontal axis while the x-ray receiver remains stationary. Slice images of a compressed breast can be generated in this manner using 2D x-ray projections acquired from different directions.

A disadvantage of these known x-ray diagnostic apparatuses for mammography examinations is that they are designed for special examination methods, and thus only limited adjustments of the component relative to one another are possible.

SUMMARY OF THE INVENTION

An object of the present invention is to provide an x-ray diagnostic apparatus for mammography examinations of the above described type that can be used universally.

According to the invention, this object is achieved by an x-ray diagnostic apparatus for mammography examinations having a support arm which is supported in a bearing such that it can pivot around a substantially horizontal axis, and on which are arranged an arm provided with an x-ray source, a mounting provided with an x-ray receiver and a compression device, such that the arm, the mounting and the compression device can be mutually pivoted with the support arm around the horizontal axis, wherein in addition the arm and the mounting can be pivoted relative to the mounting and the compression device around the horizontal axis. Due to the inventive structure of the x-ray diagnostic apparatus, it is possible to acquire medio-lateral oblique and lateral exposures of a compressed breast by pivoting the support arm around the horizontal axis, with the x-ray source, the x-ray receiver and the compression device being mutually pivoted. In addition, the possibility exists to pivot only the arm with the x-ray source and the mounting with the x-ray receiver relative to the stationary breast compressed by the compression device, in order to acquire x-ray exposures of the compressed breast from various directions for tomosynthesis. Moreover, it enables the inventive x-ray diagnostic apparatus to pivot only the arm provided with the x-ray source relative to the stationary mounting provided with the x-ray receiver and the compression device, in order to acquire x-ray exposures of the compressed breast for the stereotactic biopsy. A versatile range of use thus results from the inventive design of the x-ray diagnostic apparatus.

In an embodiment of the invention, the arm provided with the x-ray source and the mounting provided with the x-ray receiver can be coupled with one another such that they can be mutually pivoted, relative to the compression device, around the horizontal axis. In this manner it is ensured that the arm and the mounting move synchronously around the compressed breast for the acquisition of 2D projections of the compressed breast for tomosynthesis. The coupling can be, for example, a mechanical coupling of the arm with the mounting.

In an embodiment of the invention, the x-ray diagnostic apparatus has a control device to control the pivot movements of the support arm, the arm and the mounting, to control the mutual pivoting of the arm and the mounting relative to the compression device, and an image computer, in particular for the image reconstruction in tomosynthesis from x-ray exposures of the compressed breast to be examined acquired from different directions.

In another embodiment of the invention, the pivot movements of the support arm, the arm and/or the mounting are motorized, and the coupling between the arm and the mounting can be realized such that the drive motor for the pivot movements of the arm and the drive motor for the pivot movements of the mounting are activated by the control device to synchronize the pivot movements of the arm and the pivot movements of the mounting, such that a central ray originating from the ray source always strikes essentially perpendicularly on the center of the reception surface of the x-ray receiver.

In another embodiment of the invention a housing for the x-ray source and/or the x-ray receiver is dimensioned such that the pivot movements of the respective components of the x-ray diagnostic apparatus can be executed in the housing. The housing or housings is/are preferably shaped like annular sectors. In an advantageous manner, the housings form a collision protection for patients to be examined with the x-ray diagnostic apparatus, since the movements of the components take place within the housings (dependent on the respective examination) and thus a collision between the respective components and a body part of the patient is prevented.

Alteratively, in another embodiment of the invention a protective shield is provided for the x-ray source: and/or the x-ray receiver, the protective shield being dimensioned such that the pivot movements of the respective components of the x-ray diagnostic apparatus can be executed behind the protective shield. The protective shield or shield is/are preferably formed of Plexiglas® and are shaped like annular sectors. In this alternative as well, the protective shield forms a collision protection for patients to be examined with the x-ray diagnostic apparatus, since the movements of the components take place behind the protective shield (dependent on the respective examination) and thus a collision between the respective components and a body part of the patient is prevented.

In a further embodiment of the invention the compression device is fixed with the support arm, i.e. the compression device cannot be pivoted relative to the support arm. However, the connection between the compression device and the support arm is a detachable connection, such that (depending on the examination method) the compression device or even only parts of the compression device can be exchanged.

According to an embodiment of the invention, the compression device has an upper compression plate and a lower compression plate that are x-ray-transparent and can be displaced relative to one another.

In another embodiment of the invention, the x-ray diagnostic apparatus has a stand on which the bearing of the support arm for the adjustment to the size of a patient is arranged such that can be displaced. The vertical displacement of the bearing is normally motorize, but it can also be manually executable.

The x-ray source on the arm can be arranged such that it can be displaced along the arm relative to the compression device, and/or the x-ray receiver on the mounting is arranged such that it can be displaced along the mounting relative to the compression device. In this manner, the possibility to acquire enlarged x-ray exposures of the compressed breast exist by suitable displacement of the x-ray source and/or of the x-ray receiver.

DESCRIPTION OF THE DRAWINGS

FIG. 1 shows an x-ray diagnostic apparatus for mammography examinations according to the invention.

FIGS. 2 through 5 respectively show operating modes of the x-ray diagnostic apparatus of FIG. 1 in front views.

DESCRIPTION OF THE PREFERRED EMBODIMENTS

Figure 6:
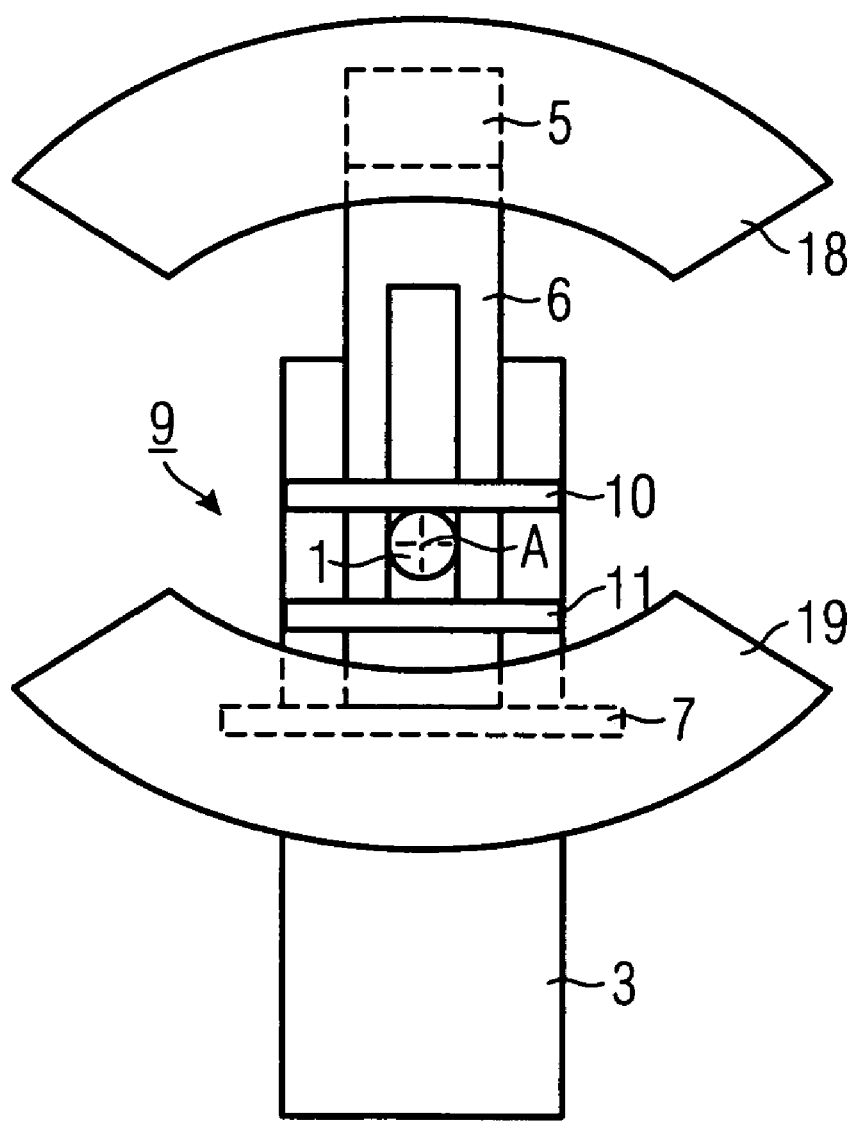
FIGS. 6 And 7 show the inventive x-ray diagnostic apparatuses with a collision shield.

In an exemplary embodiment, the x-ray diagnostic apparatus for mammography examination shown in FIG. 1 has a support arm 1 which, in a bearing 2, is positioned such that it can be pivoted around a substantially horizontal axis A (double arrow a). The bearing 2 is disposed on a stand 3 and, as indicated with the double arrow b, is vertically displaceable in a guide 4. The vertical displacement of the bearing 2 can ensue (in a manner not shown but known) manually, with motorized support or purely motorized.

An arm 6 provided with an x-ray source 5, a mounting provided with an x-ray receiver 7 and a compression device 9 are arranged on the support arm 1. The x-ray receiver 7 can be an x-ray film, an x-ray image intensifier or even a planar image detector, for example for tomosynthesis. The compression device 9, which has an upper and lower 11 x-ray-transparent compression plates 10 and 11, is fixed with the support arm 1. In the exemplary embodiment the compression device 9 can be pivoted around the axis A together with the support arm 1. A pivoting of the compression device relative to the support arm 1 is not provided in the case of the present exemplary embodiment. However, the fixed connection of the compression device 9 with the support arm 1 does not preclude an exchange of the compression device 9 with another compression device that is better suited for an examination case. Rather, the compression device is arranged on the support arm 1 by means of a detachable connection, such that a faster exchange of the compression device 9 with another is possible. In the exemplary embodiment shown in FIG. 1, the lower compression plate 11 is fixed and the upper compression plate 10 can be displaced relative to the lower compression plate 11. A female breast 12 compressed with the compression device 9 is shown in FIG. 1 in a schematic manner. The compression device 9 is preferably arranged on the support arm 1 such that the axis A is at least significantly aligned with the central breast axis of the compressed breast 12.

In the exemplary embodiment, both the arm provided with the x-ray source 5 and the mounting 8 provided with the x-ray receiver 7 can be pivoted around the axis A relative to the support arm 1 and the compression device 9. The arm 6, like the mounting 8, can be correspondingly pivoted (in a manner not shown), for example by means of bearings on which the support arm 1 is supported. The arm 6 thus can be pivoted around the axis A relative to the support arm 1, the mounting 8 and the compression device 9. In the exemplary embodiment, the mounting 8 likewise can be pivoted around the axis A relative to the support arm 1, the arm 6 and the compression device 9. The pivot movements of the support arm 1, the arm 6 and the mounting 8 are motorized in the case of the present exemplary embodiment. For this purpose, electromotors 13 through 15 are provided on the x-ray diagnostic apparatus. Based on inputs effected on a control console 16, the activation of the motors ensues via a computer installed as a control device 17, which is connected with the electromotors 13 through 15 in a manner not shown.

Moreover in the exemplary embodiment the x-ray source 5 is arranged on the arm 6 such that it can be displaced along the arm 6 (double arrow c) in the direction of the support arm 1 and the x-ray receiver 7 is arranged on the mounting 8 such that it can be displaced along the mounting 8 in the direction of the support arm 1. The displacement preferably is motorized, controlled by the control device 17. The electromotors necessary for this are not explicitly shown in the figures. The displacement can also ensue manually. In this manner, enlarged x-ray exposures of the compressed breast 12 can be acquired.

Front views of various operating forms of the x-ray diagnostic apparatus from FIG. 1 are shown in FIGS. 2 through 5, which illustrate the utility of the x-ray diagnostic apparatus for various examination modes.

An operating mode is shown in FIG. 2 In which the compression device 9 and the x-ray receiver 7 are held stationary and only the arm 6 provided with the x-ray source 5 is pivoted relative to the support arm 1 by means of the electromotor 14 around the axis A running horizontally. This pivoting of the arm 6 provided with the x-ray source 5 relative to the support arm 1, the x-ray receiver 7 and the compression device 9 is, for example, of use for a stereotactic biopsy, since in this case given a stationary examination subject (namely the breast 12 not shown in FIG. 2), spatial information of tissue of interest can be acquired from x-ray exposures of the breast from different pivot angles in order to implement the tissue. The representation of the acquire x-ray exposures on a viewing device (not shown) as well as the determination of the spatial information ensue with the aid of an image computer 21.

In FIG. 3, an operating form of the x-ray diagnostic apparatus is shown in which the arm 6 provided with the x-ray source 5 and the mounting 8 provided with the x-ray receiver 7 are pivoted around the axis A relative to the support arm 1 and the stationary compression device 9. The pivot movement of the arm 6 and the mounting 8 are thereby synchronized, which means the control device 17 controls the electromotors 14 and 15 such that, upon pivoting of the arm 6 and the mounting 8, the alignment of the x-ray source 5 relative to the x-ray receiver 7 always remains the same, such that a central beam originating from the x-ray source 5 always strikes perpendicularly on the middle of the reception surface of the x-ray receiver 7. In the exemplary embodiment, a coupling of the arm 6 and the mounting 8 thus ensues via the control device 17 and the electromotors 14 and 15 in order to achieve that these are mutually pivoted relative to the support arm 1 and the compression device 9 around the axis A running horizontally. In a modification of this embodiment, the coupling of the arm 6 and the mounting 8 can also be a detachable mechanical coupling, whereby in the case of coupling the electromotor 14 preferably effects the pivot movements of the components coupled with one another. Such a mechanical coupling can, for example ensue such that one or more brackets that can be detachably locked to the mounting 8 in a corresponding device are present on the arm 6. The operating form of the x-ray diagnostic apparatus shown in FIG. 3 is particularly suitable for tomosynthesis, in that the x-ray source 5 and the x-ray receiver 7 move around the subject (in the present case the breast 12 not shown in FIG. 3) located stationary in space, whereby 20 projections of the breast 12 are acquired from different directions in order to reconstruct from these slice images or a volume data set with the aid of an image computer 21. A corresponding reconstruction method is, for example, specified in German OS 198 42 944.

This operating mode is particularly suitable for tomosynthesis and is characterized by a larger image field that results from the coupled movement of x-ray source 5 and the x-ray receiver 7 than with fixed x-ray receiver 7 as described, for example, in U.S. Pat. No. 5,872,828.

A further advantage is that the x-ray receiver 7 is essentially always aligned perpendicularly to the central ray, such that an essentially uniform exposure of the x-ray receiver 7 always results without gradient of the intensity in 2D projections from different angles provided for tomosynthesis.

In FIGS. 4 and 5, operating form of the x-ray diagnostic apparatus is illustrated in which only the support arm 1 is pivoted with the aid of the electromotor 13 around the horizontal axis, while the alignment of the x-ray source 5, the x-ray receiver 7 and the compression device 9 thereby remains the same relative to one another. This operating mode is particularly suitable for medio-lateral oblique and lateral exposures of the breast compressed with the compression device 9.

In all operating modes, the scatter radiation is suppressed since a separation between the lower compression plate 11 and the x-ray receiver 7 is present as a result of design (air gap technique). For further reduction of the scatter radiation, scattered-ray grids can be used in a known manner. Due to the small separation between the lower compression plate 11 and the x-ray receiver 7, a better spatial resolution is moreover attained via a slight enlargement. This is particularly advantageous in tomosynthesis is using a planar image detector, since there it is to be expected that, due to the high data rate, combined detector pixels (known as pixel binning) must be handled.

An embodiment of the inventive x-ray diagnostic apparatus is shown in FIG. 6 wherein the apparatus is provided with a collision protection in the form of a annular sector-shaped housing 18 for the x-ray source 5 as well as a annular sector-shaped housing 19 for the x-ray receiver 7. The annular sector-shaped housings preferably are arranged (in a manner not shown) on the stand 3 and are dimensioned and executed such that the pivot movements of the x-ray source 8 arranged on the arm 6 are performed in the housing 18 and the pivot movements of the x-ray receiver 7 arranged on the mounting 8 are performed in the housing 19. This prevents an accidental collision between a patient positioned for an examination at the x-ray diagnostic apparatus and the x-ray source 5 or the x-ray receiver 7, which can lead to an injury of the patient.

Figure 7:
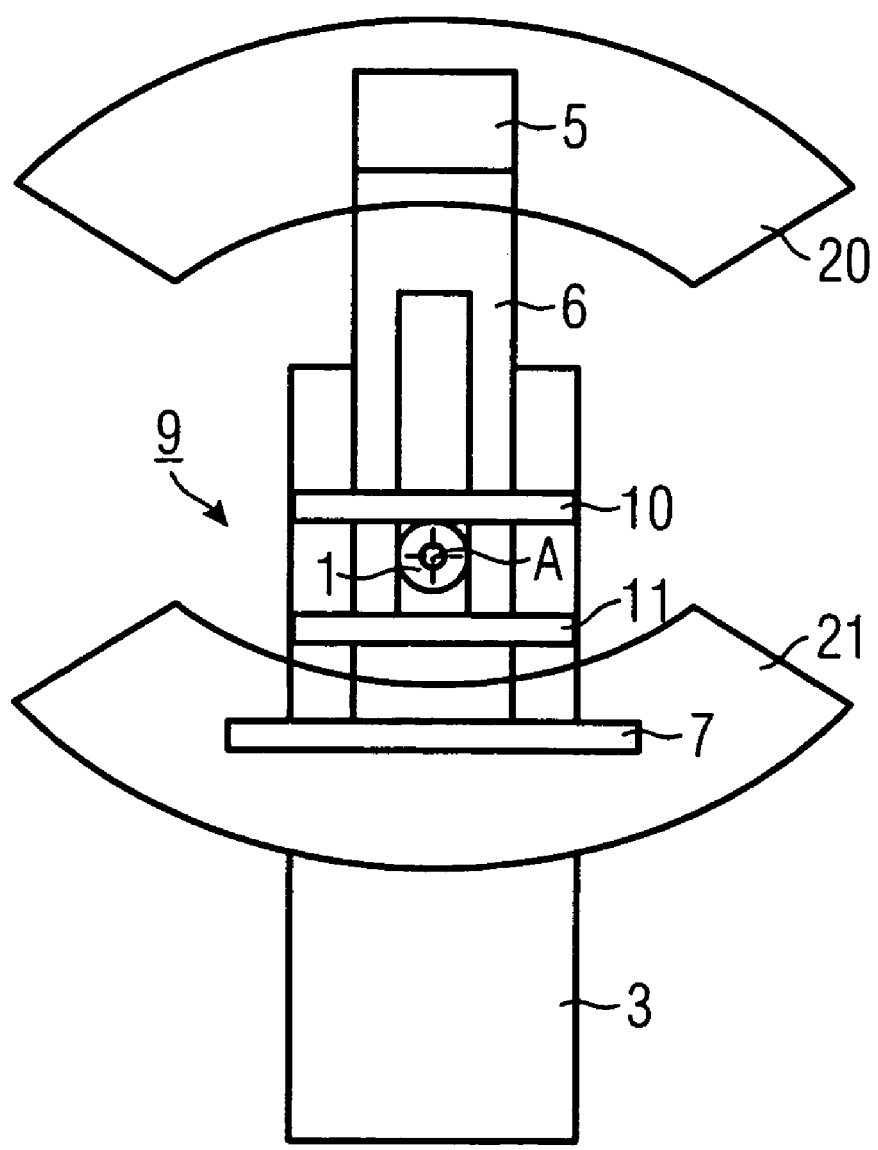

An alternative embodiment for a collision protection is shown in FIG. 7. Annular sector-shaped protective shields 20, 21 fashioned of Plexiglas® are thereby arranged in front of the x-ray source 5 and the x-ray receiver 7. The annular sector-shaped protective shields are preferably arranged (in a manner not shown) on the tripod 3 and dimensioned and executed such that the pivot movements of the x-ray source 5 arranged on the arm 6 are performed behind the protective shield 20 and the pivot movements of the x-ray receiver 7 arranged on the mounting 8 are performed behind the protective shield 21. A prevented collision between a patient positioned for an examination at the x-ray diagnostic apparatus and the x-ray source 5 or the x-ray receiver 7 also can be prevented, which can lead to an injury of the patient occurs in an accident manner.

The embodiments described above are only exemplary. For example, the pivot movements of the support arm 1, the arm 6 and the mounting 8 do not necessarily have to be motorized, but rather can ensue manually or can be supported in a motorized manner. The motor 15 for the mounting 8 can also be omitted entirely when, for example, a mechanical coupling between the arm 6 and the mounting 8 is present in order to mutually pivot the arm 6 and the mounting 8 relative to the compression device 9.

Furthermore, the motor 14 does not necessarily have to be arranged on the support arm 1. The motor, for example, can be arranged in the bearing 2 or the tripod 3, as can the motor 13. In this case, corresponding gears are provided in order to enable the pivot movements of the components.

Although modification and changes may be suggested by those skilled in the art, it is the intention of the inventor to embody within the patent warranted hereon all changes and modifications as reasonably and properly come within the scope of his contribution to the art.

I claim as my invention:

1. An X-ray diagnostic apparatus for mammography examinations, comprising:
   a support arm supported at a bearing allowing rotation of said support arm around a substantially horizontal axis;
   a further arm attached to said support arm with an x-ray source mounted on said further arm;
   a mounting attached to said support arm with a radiation receiver attached to said mounting;
   a compression device attached to said support arm; and
   said support arm allowing co-rotation of said further arm, said mounting and said compression device with said support arm around said substantially horizontal axis, and additionally allowing rotation of said further arm and said mounting relative to said compression device around said substantially horizontal axis, and allowing rotation of said further arm relative to said mounting and said compression device around said substantially horizontal axis.

2. An X-ray diagnostic apparatus as claimed in claim 1 comprising a coupling for coupling said further arm and said mounting together, allowing rotation together of said further arm and said mounting relative to said compression device around said substantially horizontal axis.

3. An X-ray diagnostic apparatus as claimed in claim 1 comprising a control device connected to said support arm, said further arm and said mounting for controlling at least rotation of said further arm and said mounting relative to said compression device, and an image computer connected to said radiation receiver for receiving image data therefrom, said image computer reconstructing an image of the breast by tomosynthesis from X-ray exposures obtained with said X-ray source and said radiation receiver disposed at a plurality of different directions relative to the breast.

4. An X-ray diagnostic apparatus as claimed in claim 1 comprising a motor connected to said support arm for rotating said support arm around said substantially horizontal axis.

5. An X-ray diagnostic apparatus as claimed in claim 1 comprising a motor connected to said further arm for controlling rotation of said further arm around said substantially horizontal axis.

6. An X-ray diagnostic apparatus as claimed in claim 1 comprising a motor connected to said mounting for controlling rotation of said mounting around said substantially horizontal axis.

7. An X-ray diagnostic apparatus as claimed in claim 1 comprising a housing in which said X-ray source is disposed, said housing having dimensions allowing rotation of said X-ray source on said further arm around said substantially horizontal axis within said housing.

8. An X-ray diagnostic apparatus as claimed in claim 7 wherein said housing has a shape comprising an annular segment.

9. An X-ray diagnostic apparatus as claimed in claim 1 comprising a housing in which said Radiation receiver is disposed, said housing having dimensions allowing rotation of said Radiation receiver on said further arm around said substantially horizontal axis within said housing.

10. An X-ray diagnostic apparatus as claimed in claim 9 wherein said housing has a shape comprising an annular segment.

11. An X-ray diagnostic apparatus as claimed in claim 1 comprising a protective shield in which said X-ray source is disposed, said protective shield having dimensions allowing rotation of said X-ray source on said further arm around said substantially horizontal axis within said protective shield.

12. An X-ray diagnostic apparatus as claimed in claim 11 wherein said protective shield is comprised of Plexiglas®.

13. An X-ray diagnostic apparatus as claimed in claim 11 wherein said protective shield has a shape comprising an annular segment.

14. An X-ray diagnostic apparatus as claimed in claim 1 comprising a protective shield in which said Radiation receiver is disposed, said protective shield having dimensions allowing rotation of said Radiation receiver on said further arm around said substantially horizontal axis within said protective shield.

15. An X-ray diagnostic apparatus as claimed in claim 14 wherein said protective shield is comprise of Plexiglas®.

16. An X-ray diagnostic apparatus as claimed in claim 14 wherein said protective shield has a shape comprising an annular segment.

17. An X-ray diagnostic apparatus as claimed in claim 1 wherein said compression device is fixed attached to said support arm.

18. An X-ray diagnostic apparatus as claimed in claim 1 wherein said compression device comprises an upper compression plate and a lower compression plate, at least one of said compression plates being displaceable relative to the other of said compression plates.

19. An X-ray diagnostic apparatus as claimed in claim 1 comprising a stand to which said bearing for said support arm is attached, allowing vertical displacement of said bearing and said support arm attached thereto.

20. An X-ray diagnostic apparatus as claimed in claim 1 wherein said X-ray source is attached to said further arm allowing displacement of said X-ray source along said further arm.

21. An X-ray diagnostic apparatus as claimed in claim 1 wherein said radiation receiver is attached to said mounting allowing displacement of said radiation receiver along said mounting.

* * * * *